US012550948B2

(12) United States Patent
Hejazi et al.

(10) Patent No.: US 12,550,948 B2
(45) Date of Patent: Feb. 17, 2026

(54) PRESSURIZED AEROSOL DELIVERY DEVICE

(71) Applicant: RAI Strategic Holdings, Inc., Winston-Salem, NC (US)

(72) Inventors: Vahid Hejazi, Concord, NC (US); William Eugene Rabbitt, Chesterland, OH (US); Robert Soreo, Cleveland Heights, OH (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 761 days.

(21) Appl. No.: 17/891,719

(22) Filed: Aug. 19, 2022

(65) Prior Publication Data

US 2024/0057691 A1 Feb. 22, 2024

(51) Int. Cl.
*A24F 42/60* (2020.01)
*A24F 7/00* (2006.01)
(Continued)

(52) U.S. Cl.
CPC ................ *A24F 42/60* (2020.01); *A24F 7/00* (2013.01); *A24F 42/20* (2020.01);
(Continued)

(58) Field of Classification Search
CPC .......... A24F 40/60; A24F 40/20; A24F 40/50; A24F 40/40; A24F 40/00; A24F 7/00
See application file for complete search history.

(56) References Cited

U.S. PATENT DOCUMENTS 4,393,884 A 7/1983 Jacobs
5,996,903 A 12/1999 Asai et al.
(Continued)

FOREIGN PATENT DOCUMENTS

CN 206423575 8/2017
EP 1 170 061 A2 1/2002
(Continued)

OTHER PUBLICATIONS

International Search Report issued in PCT Application No. PCT/IB2023/058182, mailed Jan. 3, 2024, 6 pages.
(Continued)

*Primary Examiner* — Alex B Efta
(74) *Attorney, Agent, or Firm* — Womble Bond Dickinson (US) LLP

(57) ABSTRACT

The present disclosure provides an aerosol delivery device comprising an aerosol canister containing pressurized aerosol, a metering valve, a mouthpiece, and an actuating assembly located in the mouthpiece. The actuating assembly comprises a button and an actuator and is configured to transform a button force applied to the button along a first path into an actuating force applied to the actuator along a second path, the first and second paths being noncollinear so as to actuate the metering valve to release at least a portion of the pressurized aerosol from the canister through the mouthpiece. In some implementations, the button and the actuator may comprise respective gear racks, and the actuating assembly may further include at least one pinion gear configured to engage the respective button and actuator gear racks. The actuating assembly may also include a nozzle insert configured to create a desired ejection pattern through the mouthpiece.

18 Claims, 6 Drawing Sheets

(51) Int. Cl.

| | |
|---|---|
| ***A24F 42/20*** | (2020.01) |
| ***A61M 15/00*** | (2006.01) |
| ***A61M 15/06*** | (2006.01) |
| ***B05B 1/34*** | (2006.01) |

(52) U.S. Cl.
CPC ........ *A61M 15/0065* (2013.01); *A61M 15/06* (2013.01); *B05B 1/34* (2013.01)

(56) References Cited

U.S. PATENT DOCUMENTS

| | | | | |
|---|---|---|---|---|
| 8,578,942 | B2 | 11/2013 | Schennum | |
| 8,998,483 | B2 | 4/2015 | Friend et al. | |
| 9,050,431 | B2 | 6/2015 | Turner et al. | |
| 9,770,055 | B2 | 9/2017 | Cameron et al. | |
| 9,848,648 | B2 | 12/2017 | Memari et al. | |
| 9,867,398 | B2 | 1/2018 | Guo et al. | |
| 9,936,737 | B2 | 4/2018 | Cameron et al. | |
| 9,962,507 | B2 | 5/2018 | Germinario et al. | |
| 10,004,259 | B2 | 6/2018 | Sebastian et al. | |
| 2006/0196518 | A1 | 9/2006 | Hon | |
| 2008/0084134 | A1 | 4/2008 | Morita et al. | |
| 2008/0177246 | A1* | 7/2008 | Sullivan .................. | A61M 5/30 604/116 |
| 2009/0151717 | A1 | 6/2009 | Bowen et al. | |
| 2011/0048414 | A1* | 3/2011 | Hoekman ............. | A61M 31/00 128/200.23 |
| 2011/0290249 | A1* | 12/2011 | Schennum ............ | A61M 15/06 128/202.21 |
| 2012/0090628 | A1* | 4/2012 | Turner ................ | A61M 15/009 131/273 |
| 2013/0213419 | A1 | 8/2013 | Tucker et al. | |
| 2013/0319404 | A1 | 12/2013 | Feriani et al. | |
| 2014/0238423 | A1 | 8/2014 | Tucker et al. | |
| 2014/0261487 | A1 | 9/2014 | Chapman et al. | |
| 2015/0013696 | A1* | 1/2015 | Plojoux ................... | A24F 40/40 131/328 |
| 2015/0034103 | A1 | 2/2015 | Hon | |
| 2015/0101606 | A1 | 4/2015 | White | |
| 2015/0117841 | A1 | 4/2015 | Brammer et al. | |
| 2015/0238423 | A1 | 8/2015 | Wertz et al. | |
| 2015/0245669 | A1 | 9/2015 | Cadieux et al. | |
| 2016/0007649 | A1* | 1/2016 | Sampson .................. | A24F 7/04 131/187 |
| 2016/0213866 | A1 | 7/2016 | Tan | |
| 2016/0271347 | A1 | 9/2016 | Raichman | |
| 2016/0366946 | A1 | 12/2016 | Murison et al. | |
| 2017/0042241 | A1 | 2/2017 | Murison et al. | |
| 2017/0064997 | A1 | 3/2017 | Murison et al. | |
| 2017/0157341 | A1 | 6/2017 | Pandya et al. | |
| 2017/0238608 | A1 | 8/2017 | Matsumoto et al. | |
| 2017/0303594 | A1 | 10/2017 | Cameron et al. | |
| 2017/0368273 | A1 | 12/2017 | Rubin | |
| 2018/0038838 | A1 | 2/2018 | Karancsi et al. | |
| 2018/0090923 | A1 | 3/2018 | Li et al. | |
| 2018/0153217 | A1 | 6/2018 | Liu et al. | |
| 2018/0161525 | A1 | 6/2018 | Liu et al. | |
| 2018/0169691 | A1 | 6/2018 | Macloughlin et al. | |
| 2018/0289076 | A1* | 10/2018 | Manca .................. | B05B 7/2464 |
| 2019/0014819 | A1 | 1/2019 | Sur | |
| 2019/0037923 | A1* | 2/2019 | Shenkal ................ | A24F 40/485 |
| 2019/0125987 | A1 | 5/2019 | Germinario et al. | |
| 2019/0208823 | A1* | 7/2019 | Raichman ............ | A61M 11/042 |
| 2020/0276398 | A1 | 9/2020 | Hebrank et al. | |

FOREIGN PATENT DOCUMENTS

| | | |
|---|---|---|
| EP | 2 575 938 B1 | 7/2014 |
| EP | 3228345 | 10/2017 |
| EP | 3272237 | 1/2018 |
| EP | 3278678 | 2/2018 |
| EP | 3287019 | 2/2018 |
| EP | 3298912 | 3/2018 |
| EP | 3305104 | 4/2018 |
| KR | 10-2011-0003564 A | 1/2011 |
| WO | WO2016165055 | 10/2016 |
| WO | WO2017051181 | 3/2017 |
| WO | WO2017063256 | 4/2017 |
| WO | WO2017149165 | 9/2017 |
| WO | WO2017175218 | 10/2017 |
| WO | WO2017201710 | 11/2017 |
| WO | WO2017201716 | 11/2017 |
| WO | WO2017202014 | 11/2017 |
| WO | WO2017206022 | 12/2017 |
| WO | WO2017206480 | 12/2017 |
| WO | WO2017215221 | 12/2017 |
| WO | WO2018000756 | 1/2018 |
| WO | WO2018000760 | 1/2018 |
| WO | WO2018000761 | 1/2018 |
| WO | WO2018000829 | 1/2018 |
| WO | WO2018001105 | 1/2018 |
| WO | WO2018001106 | 1/2018 |
| WO | WO2018023890 | 2/2018 |
| WO | WO2018040380 | 3/2018 |
| WO | WO2018053955 | 3/2018 |
| WO | WO2018058883 | 4/2018 |
| WO | WO2018058884 | 4/2018 |
| WO | WO2018095312 | 5/2018 |
| WO | 2021/062560 A1 | 4/2021 |

OTHER PUBLICATIONS

Ding et al., “Surface acoustic wave microfluidics”, The Royal Society of Chemistry, Issue 18, Jul. 2013, pp. 3626-3649. Retrieved from the Internet: <DOI: 10.1039/c31c50361e>.

Yeo & Friend, “Ultrafast microfluidics using surface acoustic waves”, American Institute of Physics, vol. 3, Issue 1, 2009, pp. 1-23. Retrieved from the Internet <URL: https://aip.scitation.org/doi/10.1063/1.3056040> <DOI: 10.1063/1.3056040>.

Qi et al., “Miniature inhalation therapy platform using surface acoustic wave microfluidic atomization”, The Royal Society of Chemistry, Issue 15, May 2009, pp. 2184-2193. Retrieved from the Internet <URL: https://pubs.rsc.org/en/content/articlelanding/2009/LC/b903575c#!divAbstract> <DOI: 10.1039/b903575c>.

Ariyakul & Nakamoto, “Olfactory Display Using a Miniaturized Pump and a SAW Atomizer for Presenting Low-volatile Scents”, IEEE Virtual Reality, Singapore, Mar. 2011, pp. 193-194.

Olszewski et al., “A silicon-based MEMS vibrating mesh nebulizer for inhaled drug delivery”, Procedia Engineering, vol. 168, 2016, pp. 1521-1524. Retrieved from the Internet <URL: https://www.sciencedirect.com/science/article/pii/S1877705816337729?via%3Dihub> <DOI: 10.1016/j.proeng.2016.11.451>.

Hawkins & Feng, “Vibrating Mesh Nebulizer Reference Design”, Microchip Technology Inc., 2016-2017, pp. 1-50.

Kesten et al., “Development of a novel digital breath-activated inhaler: Initial particle size characterization and clinical testing”, Pulmonary Pharmacology & Therapeutics, vol. 53, Carlsbad, California, USA, Dec. 2018, pp. 27-32. Retrieved from the Internet <URL: https://www.sciencedirect.com/science/article/pii/S1094553918301251?via%3Dihub> <DOI: 10.1016/j.pupt.2018.08.007>.

Sellers, W. “Asthma pressurized metered dose inhaler performance: propellant effect studies in delivery systems”, Allergy Asthma Clin Immunol, 2017. <DOI: 10.1186/s13223-017-0202-0> Retrieved from the Internet <URL: https://www.ncbi.nlm.nih.gov/pmc/articles/PMC5492461/>.

“levalbuterol 45 MCG-INHAL Metered Dose Inhaler, 200 Actuations”, MediPond, Rx, Your Affordable Drug Store. Retrieved from the Internet on Aug. 24, 2022 <URL: https://medipond.com/levalbuterol-45-mcg-inhal-metered-dose-inhaler-200-actuations.html>.

* cited by examiner

PRESSURIZED AEROSOL DELIVERY DEVICE

FIELD OF THE DISCLOSURE

The present disclosure relates to aerosol delivery devices such as smoking articles, and more particularly to aerosol delivery devices that produce aerosol (e.g., smoking articles commonly referred to heat-not-burn systems or electronic cigarettes). The smoking articles may be configured to deliver an aerosolized aerosol precursor composition, which may incorporate materials that may be made or derived from tobacco or otherwise incorporate tobacco, the precursor being capable of forming an inhalable substance for human consumption.

BACKGROUND

Many smoking articles have been proposed through the years as improvements upon, or alternatives to, smoking products based upon combusting tobacco. Example alternatives have included devices wherein a solid or liquid fuel is combusted to transfer heat to tobacco or wherein a chemical reaction is used to provide such heat source. Examples include the smoking articles described in U.S. Pat. No. 9,078,473 to Worm et al., which is incorporated herein by reference in its entirety.

The point of the improvements or alternatives to smoking articles typically has been to provide the sensations associated with cigarette, cigar, or pipe smoking, without delivering considerable quantities of incomplete combustion and pyrolysis products. To this end, there have been proposed numerous smoking products, flavor generators, and medicinal inhalers which utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al.; and U.S. Pat. App. Pub. Nos. 2013/0255702 to Griffith, Jr. et al.; and 2014/0096781 to Sears et al., which are incorporated herein by reference. See also, for example, the various types of smoking articles, aerosol delivery devices and electrically powered heat generating sources referenced by brand name and commercial source in U.S. Pat. App. Pub. No. 2015/0220232 to Bless et al., which is incorporated herein by reference. Additional types of smoking articles, aerosol delivery devices and electrically powered heat generating sources referenced by brand name and commercial source are listed in U.S. Pat. App. Pub. No. 2015/0245659 to DePiano et al., which is also incorporated herein by reference in its entirety. Other representative cigarettes or smoking articles that have been described and, in some instances, been made commercially available include those described in U.S. Pat. No. 4,735,217 to Gerth et al.; U.S. Pat. Nos. 4,922,901, 4,947,874, and 4,947,875 to Brooks et al.; U.S. Pat. No. 5,060,671 to Counts et al.; U.S. Pat. No. 5,249,586 to Morgan et al.; U.S. Pat. No. 5,388,594 to Counts et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,726,320 to Robinson et al.; U.S. Pat. No. 7,896,006 to Hamano; U.S. Pat. No. 6,772,756 to Shayan; U.S. Pat. App. Pub. No. 2009/0095311 to Hon; U.S. Pat. App. Pub. Nos. 2006/0196518, 2009/0126745, and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; and WO 2010/091593 to Hon, which are incorporated herein by reference.

Various manners and methods for assembling smoking articles that possess a plurality of sequentially arranged segmented components have been proposed. See, for example, the various types of assembly techniques and methodologies set forth in U.S. Pat. No. 5,469,871 to Barnes et al. and U.S. Pat. No. 7,647,932 to Crooks et al.; and U.S. Pat. App. Pub. Nos. 2010/0186757 to Crooks et al.; 2012/0042885 to Stone et al., and 2012/00673620 to Conner et al.; each of which is incorporated by reference herein in its entirety.

Certain types of cigarettes that employ carbonaceous fuel elements have been commercially marketed under the brand names "Premier," "Eclipse" and "Revo" by R. J. Reynolds Tobacco Company. See, for example, those types of cigarettes described in Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000). Additionally, a similar type of cigarette has been marketed in Japan by Japan Tobacco Inc. under the brand name "Steam Hot One."

In some instances, some smoking articles, particularly those that employ a traditional paper wrapping material, are also prone to scorching of the paper wrapping material overlying an ignitable fuel source, due to the high temperature attained by the fuel source in proximity to the paper wrapping material. This can reduce enjoyment of the smoking experience for some consumers and can mask or undesirably alter the flavors delivered to the consumer by the aerosol delivery components of the smoking articles. In further instances, traditional types of smoking articles can produce relatively significant levels of gasses, such as carbon monoxide and/or carbon dioxide, during use (e.g., as products of carbon combustion). In still further instances, traditional types of smoking articles may suffer from poor performance with respect to aerosolizing the aerosol forming component(s).

As such, it would be desirable to provide smoking articles that address one or more of the technical problems sometimes associated with traditional types of smoking articles. In addition, it would be desirable to provide a smoking article that is easy to use and that provides reusable and/or replaceable components.

BRIEF SUMMARY

The present disclosure relates to aerosol delivery devices and aerosol precursor consumables for use with aerosol delivery devices. The present disclosure includes, without limitation, the following example implementations:

Example Implementation 1: An aerosol delivery device comprising: an aerosol canister comprising a reservoir and a metering valve, the reservoir containing pressurized aerosol that includes an aerosol precursor composition; a mouthpiece configured to be secured to the aerosol canister; and an actuating assembly configured to actuate the metering valve to release at least a portion of the pressurized aerosol, wherein the actuating assembly is located in the mouthpiece, wherein the actuating assembly comprises a button and an actuator, and wherein the actuating assembly is configured to transform a button force applied to the button along a first path into an actuating force applied by the actuator along a second path, the first and second paths being noncollinear.

Example Implementation 2: The aerosol delivery device of Example Implementation 1, or any combination of preceding example implementations, wherein the first and second axes are substantially orthogonal with respect to each other.

Example Implementation 3: The aerosol delivery device of any one of Example Implementations 1-2, or any combination of preceding example implementations, wherein the actuating assembly transforms the button force into the actuating force via one or more gears.

Example Implementation 4: The aerosol delivery device of any one of Example Implementations 1-3, or any combination of preceding example implementations, wherein the button of the actuating assembly comprises at least one button gear rack, wherein the actuator of the actuating assembly comprises at least one actuator gear rack, and wherein the actuating assembly further includes at least one pinion gear configured to engage the at least one button gear rack and the at least one actuator gear rack to translate the actuator along the second path upon movement of the button along the first path.

Example Implementation 5: The aerosol delivery device of any one of Example Implementations 1-4, or any combination of preceding example implementations, wherein the button of the actuating assembly comprises a pair of button gear racks, wherein the actuator of the actuating assembly comprises a pair of actuator gear racks, wherein the actuating assembly further includes a pair of pinion gears, and wherein each pinions gear is configured to engage a respective button gear rack and a respective actuator gear rack to translate the actuator along the second path upon movement of the button along the first path.

Example Implementation 6: The aerosol delivery device of any one of Example Implementations 1-5, or any combination of preceding example implementations, wherein the button further includes at least one guide slot, wherein the actuating assembly further includes at least one guide pin, and wherein the guide pin and the guide slot are configured to guide the button along the first path.

Example Implementation 7: The aerosol delivery device of any one of Example Implementations 1-6, or any combination of preceding example implementations, wherein the actuating assembly further includes a nozzle insert configured to create a desired ejection pattern of the pressurized aerosol.

Example Implementation 8: The aerosol delivery device of any one of Example Implementations 1-7, or any combination of preceding example implementations, wherein the nozzle insert is configured to be inserted into an aerosol channel of the actuator.

Example Implementation 9: The aerosol delivery device of any one of Example Implementations 1-8, or any combination of preceding example implementations, wherein the nozzle insert includes a substantially conical ejection port terminating at an ejection port opening.

Example Implementation 10: The aerosol delivery device of any one of Example Implementations 1-9, or any combination of preceding example implementations, wherein the nozzle insert further includes at least one ejection channel, the ejection channel being configured to direct the pressurized aerosol into the ejection port.

Example Implementation 11: The aerosol delivery device of any one of Example Implementations 1-10, or any combination of preceding example implementations, wherein the ejection nozzle further includes at least three ejection channels, the ejection channels being configured to direct the pressurized aerosol into the ejection port.

Example Implementation 12: The aerosol delivery device of any one of Example Implementations 1-11, or any combination of preceding example implementations, wherein the at least three ejection channels comprise a staggered radial arrangement, wherein respective center axes of the ejection channels are non-coincident with a center of the ejection port opening.

Example Implementation 13 The aerosol delivery device of any one of Example Implementations 1-12, or any combination of preceding example implementations, wherein the mouthpiece includes a diverter located between the metering valve and an outlet of the mouthpiece.

Example Implementation 14: The aerosol delivery device of any one of Example Implementations 1-13, or any combination of preceding example implementations, wherein the diverter comprises a substantially V-shaped leading edge.

Example Implementation 15: The aerosol delivery device of any one of Example Implementations 1-14, or any combination of preceding example implementations, wherein the diverter comprises a substantially V-shaped trailing edge.

Example Implementation 16: The aerosol delivery device of any one of Example Implementations 1-15, or any combination of preceding example implementations, wherein the diverter comprises a substantially V-shaped leading edge and a substantially V-shaped trailing edge, and wherein the substantially V-shaped leading edge is convex with respect to the direction of flow of the pressurized aerosol and the substantially V-shaped trailing edge is concave with respect to a direction of flow of the pressurized aerosol.

Example Implementation 17: The aerosol delivery device of any one of Example Implementations 1-16, or any combination of preceding example implementations, wherein the mouthpiece is secured to the aerosol canister via a pair of securing pins that extend through the mouthpiece.

Example Implementation 18: The aerosol delivery device of any one of Example Implementations 1-17, or any combination of preceding example implementations, wherein the mouthpiece and the aerosol canister are substantially longitudinally aligned.

Example Implementation 19: The aerosol delivery device of any one of Example Implementations 1-18, or any combination of preceding example implementations, wherein the button is configured to rotate relative to the mouthpiece.

Example Implementation 20: The aerosol delivery device of any one of Example Implementations 1-19, or any combination of preceding example implementations, wherein the actuator is configured to rotate relative to the mouthpiece.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
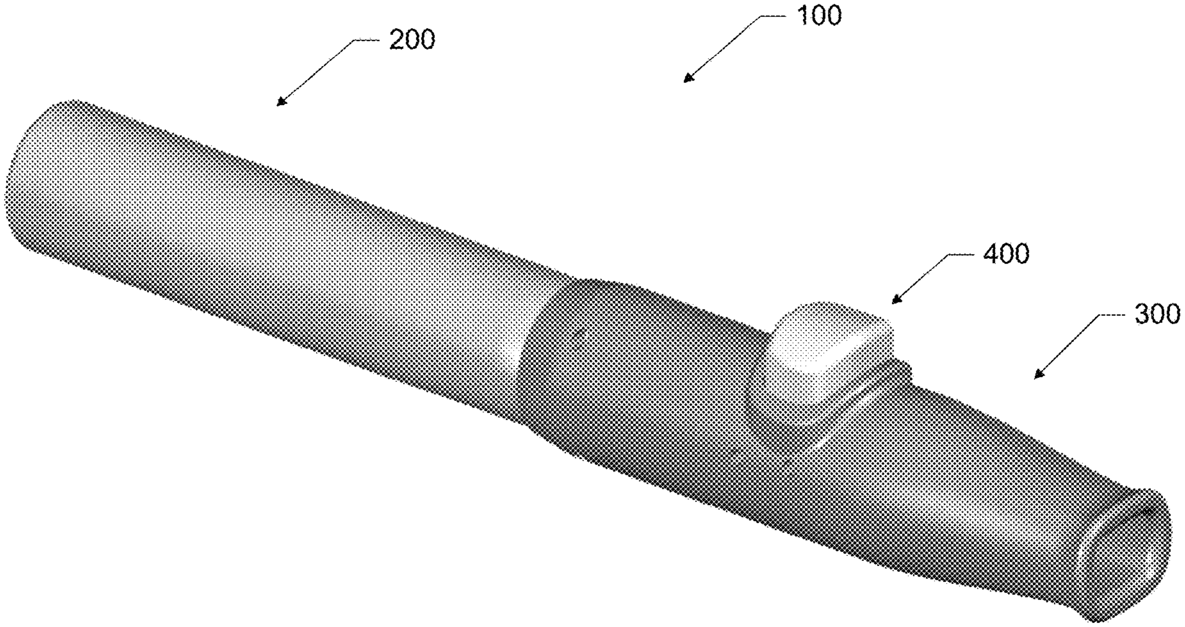
Figure 2:
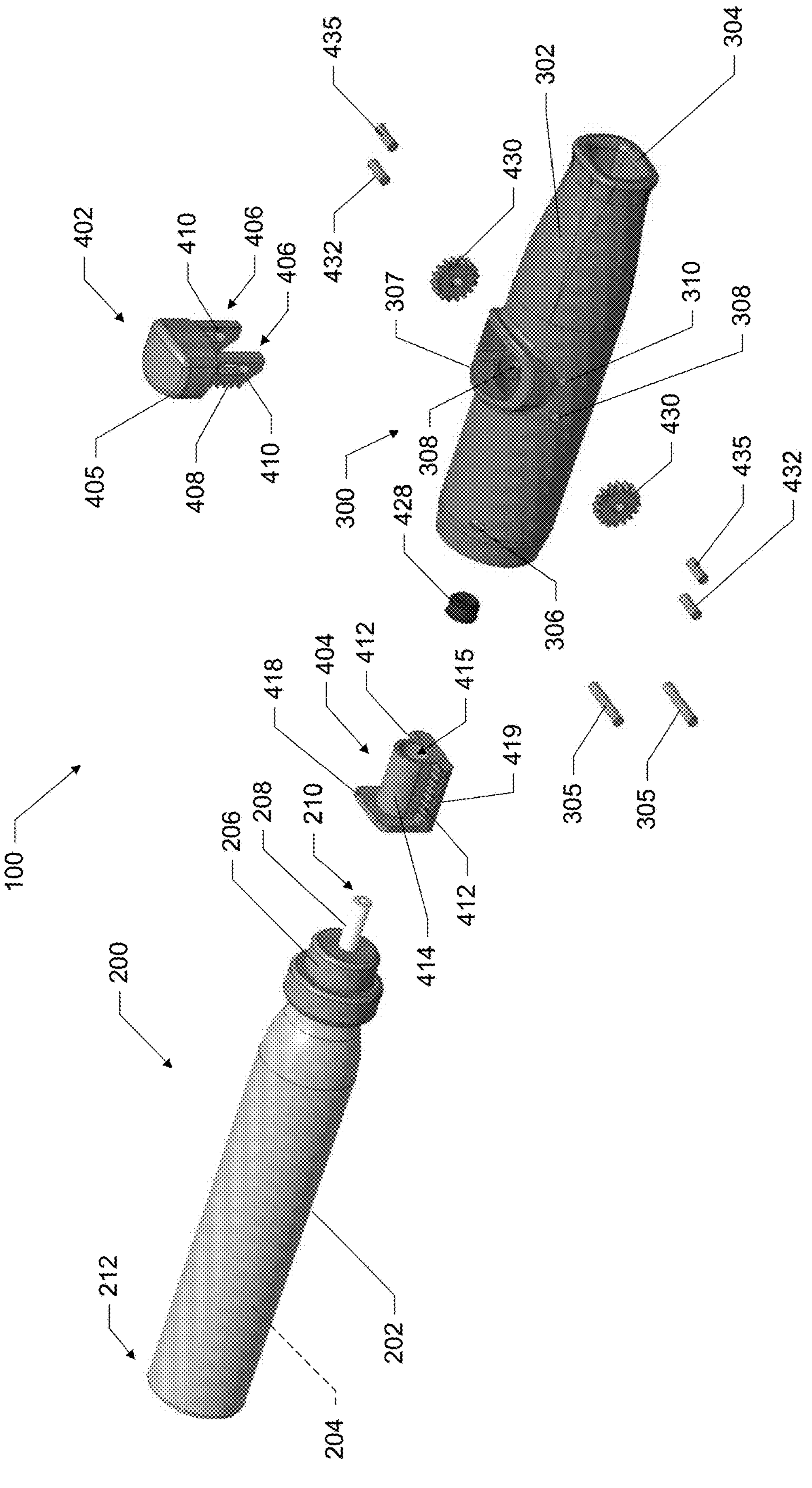
Figure 3:
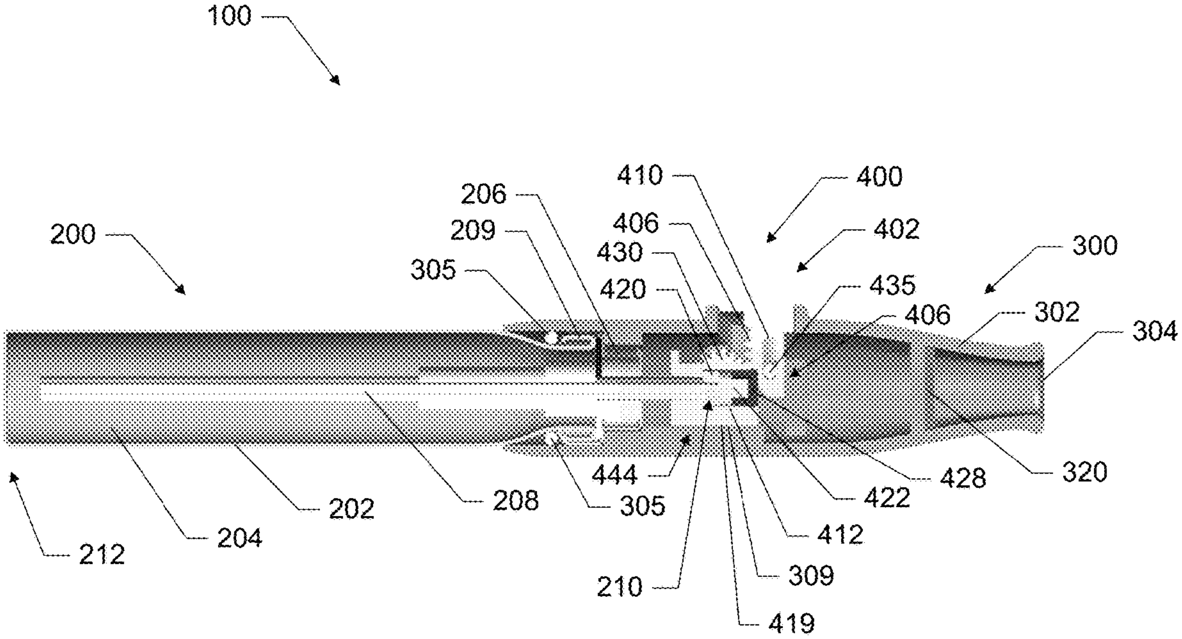
Figure 4A:
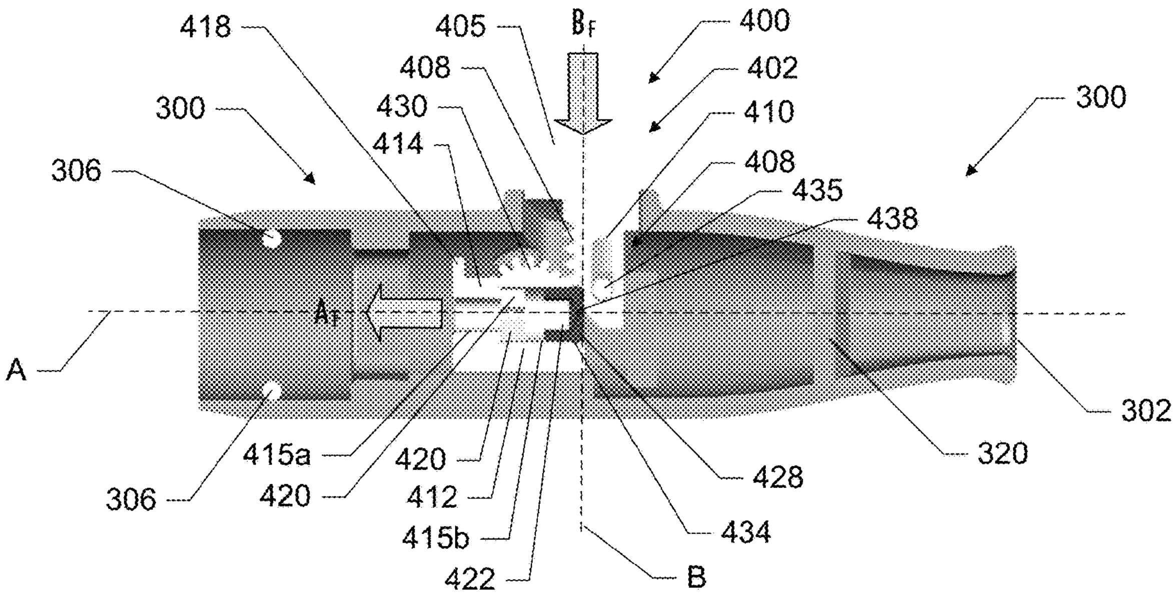
Figure 5:
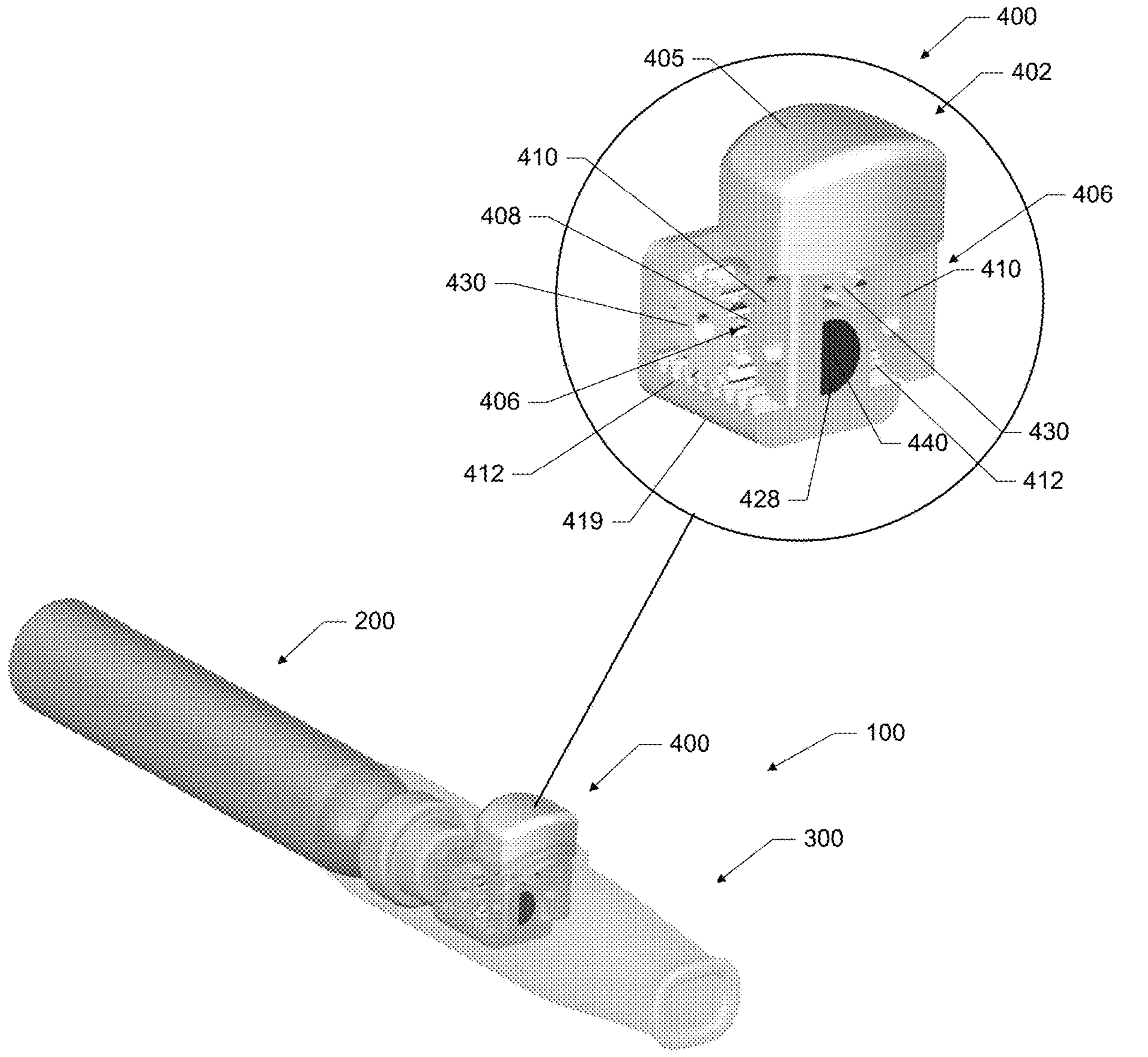
Figure 6A:
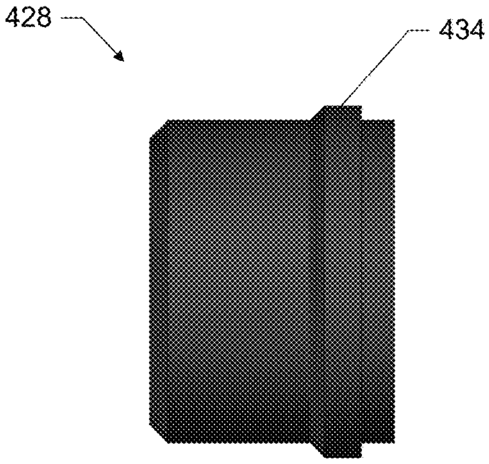
Figure 6B:
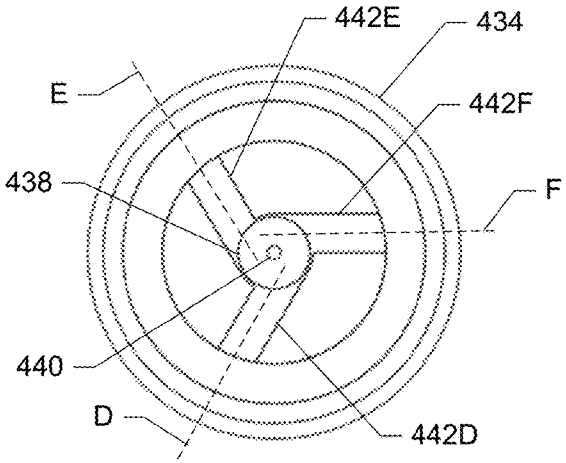
Figure 6C:
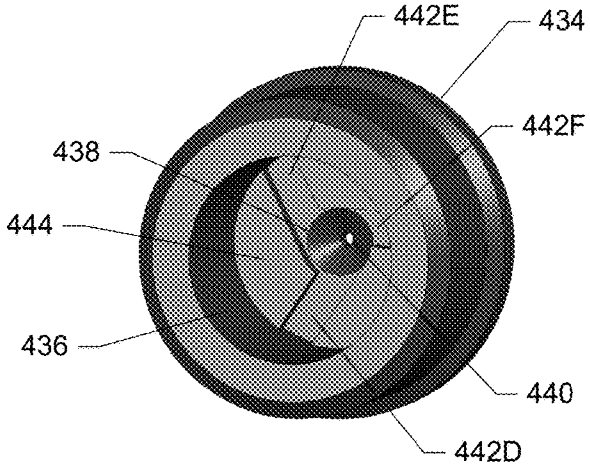

Having thus described the disclosure in the foregoing general terms, reference will now be made to the accompanying drawings, which are not necessarily drawn to scale, and wherein:

FIG. 1 is an isometric view of an aerosol delivery device, according to an example implementation of the present disclosure;

FIG. 2 is an isometric exploded view of an aerosol delivery device, according to an example implementation of the present disclosure;

FIG. 3 is a side cross-section view an aerosol delivery device, according to an example implementation of the present disclosure;

FIGS. 4A and 43B are side and top cross-section views, respectively, according to an example implementation of the present disclosure;

FIG. 5 is an isometric detailed view of an aerosol delivery device with the mouthpiece shown as transparent to facilitate illustration, according to an example implementation of the present disclosure; and FIGS. 6A, 6B, and 6C are side, schematic front, and isometric views, respectively, of a nozzle insert of an aerosol delivery device, according to an example implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, implementations of the present disclosure relate to aerosol delivery devices or vaporization devices, said terms being used herein interchangeably. Aerosol delivery devices according to the present disclosure deliver aerosolized material in the form of an inhalable substance; and components of such devices have the form of articles that most preferably are sufficiently compact to be considered hand-held devices. In some embodiments, the present aerosol delivery devices may be configured to deliver a material (preferably without combusting the material to any significant degree and/or without significant chemical alteration of the material) in the form of the inhalable substance. Preferably, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In some implementations, components of aerosol delivery devices may be generally characterized as electronic cigarettes, although they may not contain electronic components, and those electronic cigarettes most preferably incorporate tobacco and/or components derived from tobacco, and hence deliver tobacco derived components in aerosol form.

As noted, some aerosol delivery devices use electrical energy to energize a material to form an inhalable substance. For example, some aerosol delivery devices use electrical energy to heat a material to form an inhalable substance (e.g., electrically heated tobacco products), and other implementations of aerosol delivery devices use electrical energy to vibrate a material to form an inhalable substance. Still other aerosol source members use an ignitable heat source to heat a material to form an inhalable substance (e.g., carbon heated tobacco products). The material may be heated without combusting the material to any significant degree. As such, the presently disclosed subject matter may be used in relation to a variety of aerosol and/or vapor producing devices, which may include, but is not limited to, devices commonly known as e-cigarettes, heat-not-burn (HNB) devices, carbon tobacco heated products (cTHP), and electric tobacco heated products (eTHP). Non-limiting examples of such devices to which any part or all of the present disclosure may be incorporated are described in U.S. Pat. Nos. 9,839,238, 9,913,493, 10,085,485, and 10,349,674, each of which is incorporated herein in its entirety.

Components of such systems have the form of articles that are sufficiently compact to be considered hand-held devices. That is, use of components of aerosol delivery devices does not result in the production of smoke in the sense that aerosol results principally from by-products of combustion or pyrolysis of tobacco, but rather, use of those systems results in the production of vapors resulting from volatilization or vaporization of certain components incorporated therein. In some example embodiments, components of aerosol delivery devices may be characterized as electronic cigarettes, and those electronic cigarettes may incorporate tobacco and/or components derived from tobacco, and hence deliver tobacco derived components in aerosol form.

Aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating device of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure can also be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Some aerosol delivery devices comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), an atomizer, a liquid composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

The specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

In various implementations, the present disclosure provides an aerosol delivery device that delivers a pressurized aerosol to a user. One example implementation of an aerosol delivery device 100 according to the present disclosure is shown in FIG. 1. In general, the aerosol delivery device 100 of the depicted implementation includes an aerosol canister 200, a mouthpiece 300, and an actuating assembly 400. As will described in more detail below, the mouthpiece 300 of the depicted implementation is secured to the aerosol canister 200 in a semi-permanent manner using one or more press-fit pins. In other implementations, however, the mouthpiece may be releasably attached to the aerosol canister. For example, the mouthpiece of some implementations may be attached to the aerosol canister via one or more of a snap-fit, interference fit, screw thread, magnetic, and/or bayonet connection. In the depicted implementation, the aerosol canister has a general cylindrical shape with a substantially circular outer cross-section; however, the aerosol canister of other implementations may have a variety of other shapes configured to retain a pressurized aerosol.

Referring also to FIGS. 2 and 3, the aerosol canister 200 of the depicted implementation includes a body 202 defining a reservoir 204 configured to contain a pressurized aerosol. As will be described in more detail below, the pressurized aerosol comprises a liquid composition that may contain a substance made or derived from tobacco (such as, for example, nicotine), or some other substance and/or other ingredients. The aerosol canister 200 of the depicted implementation also includes a collar 206 and a one-way metering valve 208. In the depicted implementation, the collar 206 is secured to the body 202 via a crimp attachment around a folded portion 209 of the body 202, although in other implementations, the collar may be attached to the body in variety of different ways, including for example, via welded, adhered, and/or screw-fit attachment.

As shown in the figures, one end of the metering valve 208 extends into the reservoir 204, and the other end of the metering valve 208 extends through the collar 206 such that it terminates a distance away from the downstream end of the collar 206. In the depicted implementation, the metering valve 208 is configured such that when an upstream end 210 of the metering valve 208 is depressed axially (e.g., in a direction toward a distal end 212 of the aerosol canister 200) pressurized aerosol travels through the metering valve 208 and is released through the upstream end 210 of the metering valve 208. In such a manner, the metering valve 208 may be moved from a closed position to an open position. In the depicted implementation, the metering valve 208 is spring-loaded and biased into the closed position.

In the depicted implementation, the mouthpiece 300 comprises a substantially hollow body 302 that defines an outlet 304 through which the pressurized aerosol is delivered to a user. In the depicted implementation, the mouthpiece 300 is secured to the aerosol canister 200 using a pair of press-fit pins 305 that extend through corresponding openings 306 in the mouthpiece body 302. In the depicted implementation, the pins 305 are made of a metal material, such as, for example, a stainless-steel material. In other implementations, however, the pins may be made of any suitable material, including, for example, a plastic material, such as, for example, polycarbonate, polyethylene, acrylonitrile butadiene styrene (ABS), polyamide (Nylon), or polypropylene, other metal materials, such as, for example, aluminum, brass, copper, silver, gold, bronze, titanium, various alloys, etc. Other non-metal or non-plastic materials are also possible.

The pins 305 of the mouthpiece 300 are positioned downstream from the folded portion 209 of the aerosol canister body 202 such that the pins 305 secure (e.g., by trapping) the upstream end of the aerosol canister 200 inside the mouthpiece body 302. The mouthpiece 300 also includes a button opening 307 located on a top portion of the mouthpiece body 302. The button opening 307 of the depicted implementation is shaped to accommodate the outer shape of the button of the actuator, discussed in more detail below. The mouthpiece 300 further includes a guide surface 309 located in the interior of the mouthpiece body 302 proximate a lower surface of the actuator.

In the depicted implementation, the mouthpiece 300 and the aerosol canister 200 are substantially longitudinally aligned. In other implementations, however, other arrangements are possible. For example, the mouthpiece of some implementations may form an angle (e.g., an acute angle, a substantially perpendicular angle, or an obtuse angle) with respect to a longitudinal axis of the aerosol canister. In the depicted implementation, the mouthpiece 300 has an oblong outer shape with a substantially oval outer cross-section in the area proximate the outlet 304 of the mouthpiece 300 that transitions into a cylindrical outer shape with a substantially circular outer cross-section in the area proximate the pin openings 306 in the mouthpiece body 302 (e.g., in the area proximate the connection to the downstream end of the aerosol canister 200). In other implementations, however, the mouthpiece may have a variety of different shapes, including in one or both of these areas.

In the depicted implementation, the mouthpiece is constructed of a plastic material, such as, for example, polycarbonate, polyethylene, acrylonitrile butadiene styrene (ABS), polyamide (Nylon), or polypropylene. In other implementations, the mouthpiece may be made of a different material, such as, for example, a different plastic material, a metal material (such as, but not limited to, stainless steel, aluminum, brass, copper, silver, gold, bronze, titanium, various alloys, etc.), a graphite material, a glass material, a ceramic material, a natural material (such as, but not limited to, a wood material), a composite material, or any combinations thereof. As noted above, the mouthpiece of some implementations may separable from the aerosol canister. In other implementations, however, the mouthpiece may be integral with the aerosol canister.

In the depicted implementation, the actuating assembly 400 includes a button 402 and an actuator 404, which, in the depicted implementation, comprise separate parts. The button 402 of the depicted implementation includes a contact portion 405, which is configured to be activated (e.g., pressed) by a user, and a pair of extensions 406 that extend downwardly from the contact portion 405. In the depicted implementation, the contact portion 405 is configured to provide a comfortable area for a user's finger, and in particular, a user's thumb, to activate the button, for example, by pressing downward. In such a manner, the shape of the contact portion 405 of the depicted implementation has a general oblong shape. In other implementations, however, the contact portion may have any shape configured for use by a user's finger (e.g., via pressing, rotating, spinning, etc.).

Figure 4B:
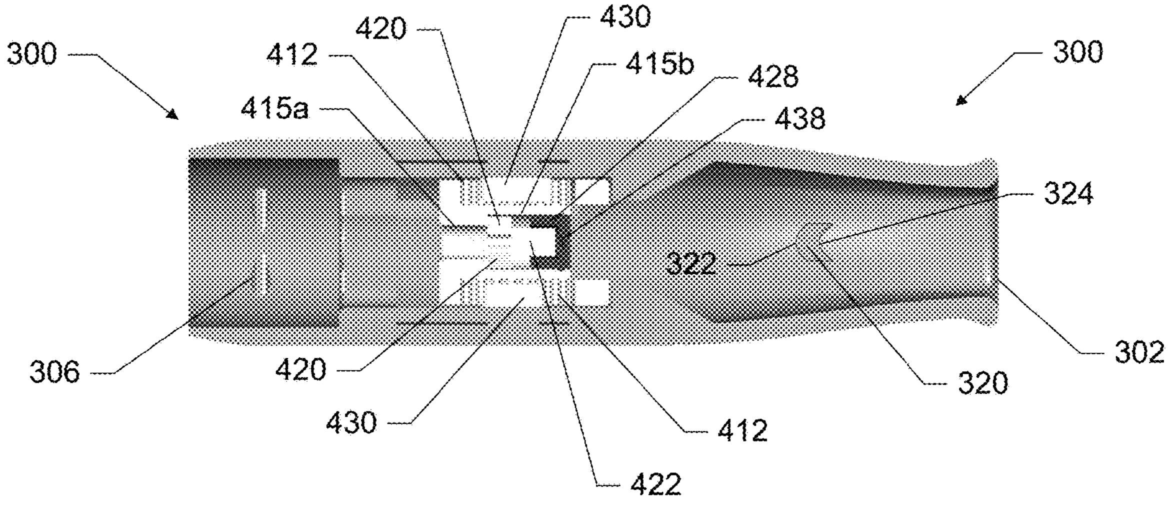

In the depicted implementation, each of the pair of extensions 406 includes a respective gear rack 408 comprising a plurality of gear teeth and a respective guide slot 410 formed through a portion of the extension 406 proximate the gear rack 408. The actuator 404 of the depicted implementation also includes a pair of gear racks 412 located on opposite sides of a main body portion 414. In the depicted implementation, the main body portion 414 defines an aerosol channel 415 that extends therethrough. The actuator 404 of the depicted implementation also includes a rear flange 418 that is substantially perpendicular to the pair of gear racks 412, as well as a bottom flange 419 below the gear racks 412. Referring in particular to FIGS. 3, 4A, 4B, and the aerosol channel 415 of the depicted implementation of the actuator 404 extends through the main body portion 414 and includes an upstream portion 415*a* and a downstream portion 415*b*, the upstream portion 415*a* having a smaller internal diameter than the downstream portion 415*b*. The actuator 404 of the depicted implementation also includes a plurality of contact features 420 located inside the main body portion 414 and positioned radially around the downstream portion 415*b* of the aerosol channel 415. As will be described in more detail below, when assembled, the contact features 420 of the depicted implementation are configured to contact the upstream end 210 of the metering valve 208.

The actuator 404 of the depicted implementation also includes cylinder feature 422 located in the main body portion 414, and in particular, substantially centrally located in the downstream portion 415*b* of the aerosol channel 415. In the depicted implementation, a nozzle insert 428 is positioned proximate the downstream end of the cylinder feature 422, the end of which is substantially aligned with the end of the downstream portion 415*b* of the aerosol channel 415. In the depicted implementation, a sealing ring 434, which extends around an outer surface of the nozzle insert 428, provides a sealing arrangement between the nozzle insert 428 and the downstream portion 415*b* of the aerosol channel 415. In such a manner, pressurized aerosol traveling through the aerosol channel 415 exits through the nozzle insert 428, which is configured to create a desired ejection pattern through the mouthpiece 300. In the depicted implementation, the nozzle insert 428 is made of an elastomeric material, such as, for example, a silicone rubber material. In other implementations, however, the nozzle insert may be made of any material, including any one or any combination of materials described herein with respect to other components of the actuating assembly and/or mouthpiece.

The actuating assembly 400 of the depicted implementation further includes a pair of pinion gears 430 and a respective pair of pinion gear pins 432. In the depicted implementation, the pinion gear pins 432 are configured for a press-fit connection into the mouthpiece body 302 through the respective gear pin openings 308 located on both sides of the mouthpiece body 302. The actuating assembly 400 also includes a pair of guide pins 435 that are configured for a press-fit connection into the mouthpiece body 302 through respective guide pin openings 310 located on both sides of the mouthpiece body and downstream from the gear pin openings 308. When assembled, each of the pinion gears 430 of the depicted implementation is configured to rotate about a respective gear pin 432 and engage respective ones of the button gear racks 408 as well as respective ones of the actuator gear racks 412, thereby forming a rack-pinion-rack gear train between the button 402 and the actuator 404. It should be noted that although in the depicted implementation the actuating assembly includes a pair of pinion gears and the button and the actuator each include a pair of gear racks, in other implementations the actuating assembly may include a single pinion gear and the button and the actuator each include a single gear rack. Likewise, although the depicted implementation includes a pair of guide slots located in the button, other implementations may include a single guide slot, which may be located in the button or another component of the actuating assembly. Still other implementations may include no guide slot.

In the depicted implementation, the components of the actuating assembly are constructed of a plastic material, such as, for example, polycarbonate, polyethylene, acrylonitrile butadiene styrene (ABS), polyamide (Nylon), or polypropylene. In other implementations, any one or any combination of the components of the actuating assembly may be made of a different material, such as, for example, a different plastic material, a metal material (such as, but not limited to, stainless steel, aluminum, brass, copper, silver, gold, bronze, titanium, various alloys, etc.), a graphite material, a glass material, a ceramic material, a natural material (such as, but not limited to, a wood material), a composite material, or any combinations thereof.

In various implementations, the actuating assembly of the present disclosure is configured to transform a button force applied along a first path into an actuating force applied along a second path. FIGS. 4A and 4B illustrate one example with respect to the actuating assembly 400 of the depicted implementation described above. In particular, when the actuating assembly 400 is fully assembled within the mouthpiece 300, the actuating assembly 400 is configured to transform a button force BF applied to the button 402 along axis A into an actuating force $A_F$ applied by the actuator 404 along axis B, which is noncollinear with axis A. In the depicted implementation, axis B is substantially orthogonal to axis A, and more particularly, axis B is substantially perpendicular to axis A. In other implementations, however, a variety of different arrangements are possible. For example, in some implementations one of the first or second paths may form an acute (or obtuse) angle with respect to the other. In other implementations, one of the first or second paths may comprise an arcuate path and the other of the first or second paths may comprise a substantially linear path. In other implementations, both the first and second paths may comprise arcuate paths.

As illustrated in the figures, when a user applies a button force BF to the button 402, the button gear racks 408 move downward in a direction substantially aligned or substantially parallel to axis B and are guided by the guide slots 410, which travel downward through the guide pins 435. The movement of the gear racks 408 in this direction causes the pinion gears 430 to rotate in a clockwise direction (with respect to the depiction in the figures), which, in turn, causes the actuator gear racks 412 to move in a direction substantially aligned or substantially parallel to axis A. Because the actuator gear racks 412 are integral with the actuator 404, the entire actuator 404 moves in this direction, guided by guide surface 309 over which the bottom flange 419 of the actuator 404 slidingly travels. As noted above, the contact features 420 of the actuator 404 are in contact with the upstream end 210 of the metering valve 208. In such a manner, when the actuator 404 moves in a direction substantially aligned or substantially parallel to axis A, the contact features 420 of the actuator 404 depress the metering valve 208, thereby releasing at least a portion of the pressurized aerosol from the aerosol canister 200 through the upstream end 210 of the metering valve 208.

It should be noted that although in the depicted implementation the actuating assembly is configured to transform a button force applied to the button along a first path into an actuating force applied by the actuator along a second path using a gear train mechanism that includes a pair of gear racks, other implementations may utilize alternative mechanisms. For example, in some implementations the actuating assembly may be configured to transform a button force along a first path into an actuating force along a second path via a gear train mechanism that does not include gear racks. In other implementations, the actuating assembly may be configured to transform a button force along a first path into an actuating force along a second path via a cam mechanism, such as, for example, a mechanism in which the button includes a cam feature configured to convert a force on the button along the first path into a force on the metering valve along the second path. In other implementations, the actuating assembly may be configured to transform a button force along a first path into an actuating force along a second path via a slider-crank mechanism, such as, for example, a mechanism in which the button rotates about an axis and a connected slider actuates the metering valve, or, alternatively, a mechanism in which the actuator rotates about an axis and is connected to a slider button. In still other implementations, the actuating assembly may be configured to transform a button force along a first path into an actuating force along a second path via a four-bar linkage mechanism.

In the depicted implementation, the actuating assembly 400 is configured such that the actuator 404 continues to depress the metering valve 208 as long as a button force acts on the button 402. As such, as long as a button force is applied to the button 402, pressurized aerosol will continue to be released from the aerosol canister 200 (at least as long as aerosol remains in the aerosol canister 200). In various implementations, the amount of pressurized aerosol contained in the aerosol canister may differ. For example, the aerosol canister of some implementations may contain enough pressurized aerosol to last a plurality (e.g., 2 or more, such as, for example, any number between approximately 2 and approximately 20, or any number above approximately 20) of typical smoking sessions. In other implementations, the aerosol canister may contain enough pressurized aerosol to last a single typical smoking session. In some implementations, the canister may include an amount of aerosol corresponding to between approximately 10 to approximately 200 puffs. For example, in some implementations, the canister may include an amount of aerosol corresponding to approximately 100 puffs or less. In some implementations, the canister may include an amount of aerosol corresponding to approximately 70 puffs or less. In some implementations, the mass of the liquid in the canister may be between approximately 5 to approximately 50 grams. For example, in some implementations, the mass of the liquid contained in the canister may be between approximately 10 grams to approximately 11 grams.

With specific reference to FIGS. 4A, 4B, when the pressurized aerosol is released from the aerosol canister 200 and through the upstream end 210 of the metering valve 208, the aerosol travels through the upstream portion 415*a* of the aerosol channel 415 and into the downstream portion 415*b* thereof. Due to the seal created by the sealing ring 434 of the aerosol insert 430, once the aerosol travels into the downstream portion 415*b* of the aerosol channel, the aerosol is forced to travel between the outer surface of the cylinder feature 422 and an inner surface 436 (see FIG. 6A) of the nozzle insert 428. In such a manner, substantially all of the pressurized aerosol released from the aerosol canister 200 travels through the nozzle insert 428. With further reference to FIGS. 6A-6C, the nozzle insert 428 of the depicted implementation comprises a cap shape that has a first end and a second end. In the depicted implementation, the first end of the nozzle insert 428 is open and the second end of the nozzle insert 428 is closed, with the exception of a substantially conical ejection port 438 that terminates at an ejection port opening 440.

In various implementations, the nozzle insert may further include at least one ejection channel configured to direct the pressurized aerosol into the ejection port. In the depicted implementation, the nozzle insert 428 includes three ejection channels 442D, 442E, and 442F that are formed on an inner surface 444 of the closed end of the aerosol insert 428. In particular, each of the ejection channels 442D, 442E, 442F of the depicted implementation is formed as a recessed area comprising a pair of spaced and substantially linear edges that begin at the inner surface 436 of the aerosol insert 428 and lead toward the ejection port 438. In the depicted implementation, the three ejection channels 442D, 442E, 442F comprise a staggered radial arrangement around the ejection port 438. In such a manner, respective center axes D, E, F of the ejection channels 442D, 442E, 442F are non-coincident with the center of the ejection port opening 440. As such, the arrangement and configuration of the one or more ejection channels are configured to create a desired ejection pattern of the pressurized aerosol through the mouthpiece. It should be noted that in other implementations, a variety of other configurations and/or arrangements of the one or more ejection channels are possible. For example, in some implementations, the one or more ejection channels may comprise a non-staggered or standard radial arrangement, such as an arrangement in which the one or more associated center axes of the one or more ejection channels are coincident with the center of the ejection port opening. In other implementations, the one or more ejection channels may represent a curved arrangement leading to the ejection port opening. For example, in some implementations the one or more ejection channels may have a spiral arrangement leading to the ejection port opening. In some implementations, one or more ejection channels may be included on the inner surface of the nozzle insert.

Referring back to FIGS. 4A and 4B, the mouthpiece 300 of the depicted implementation also includes a diverter 320 that is located between the upstream end 210 of the metering valve 208 and the outlet 304 of the mouthpiece 300. Although a variety of other locations are possible, the diverter 320 of the depicted implementation is specifically located downstream from the ejection port opening 440 of the nozzle insert 428 and upstream from the outlet 304 of the mouthpiece 300. In such a manner, the diverter 320 of the depicted implementation is configured to affect the flow of aerosol exiting the ejection port opening 440. Although a variety of arrangements and configurations are possible, the diverter 320 of the depicted implementation spans across the inside of the mouthpiece body 302 and comprises a substantially V-shaped leading edge 322, which is convex with respect to the direction of flow of the aerosol, and a substantially V-shaped trailing edge 324, which is spaced from the leading edge 322 and which is convex with respect to the direction of flow of the aerosol. As such, aerosol passing by the diverter 320 is forced to travel around (e.g., on both sides of) the diverter 320 before exiting the outlet 304 of the mouthpiece 300. Although in the depicted implementation there is one diverter located in the mouthpiece, in other implementations there may be any number of diverters, which may or may not be located in the mouthpiece and which may or may not have the same arrangement and/or configuration as the depicted diverter.

As noted above, the aerosol delivery device of the present disclosure is configured to deliver a pressurized and aerosolized aerosol precursor composition to a user. The aerosol precursor composition, sometimes referred to as an aerosol precursor liquid composition or a vapor precursor composition or "e-liquid", may comprise a variety of components, which may include, by way of example, a polyhydric alcohol (e.g., glycerin, propylene glycol, or a mixture thereof), nicotine, tobacco, tobacco extract, and/or flavorants. Representative types of aerosol precursor components and formulations are also set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor composition incorporated within the aerosol delivery system is such that the aerosol generating device provides acceptable sensory and desirable performance characteristics. For example, sufficient amounts of aerosol forming material (e.g., glycerin and/or propylene glycol) may be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating device. In one or more embodiments, about 1 ml or more, about 2 ml or more, about 5 ml or more, or about 10 ml or more of the aerosol precursor composition may be included.

In the some of the examples described above, the aerosol precursor composition comprises a glycerol-based liquid. In other implementations, however, the aerosol precursor composition may be a water-based liquid. In some implementations, the water-based liquid may be comprised of more than approximately 80% water. For example, in some implementations the percentage of water in the water-based liquid may be in the inclusive range of approximately 90% to approximately 93%. In some implementations, the water-based liquid may include up to approximately 10% propylene glycol. For example, in some implementations the percentage of propylene glycol in the water-based liquid may be in the inclusive range of approximately 4% to approximately 5%. In some implementations, the water-based liquid may include up to approximately 10% flavorant. For example, in some implementations the percentage of flavorant(s) of the water-based liquid may be in the inclusive range of approximately 3% to approximately 7%. In some implementations, the water-based liquid may include up to approximately 1% nicotine. For example, in some implementations the percentage nicotine in the water-based liquid may be in the inclusive range of approximately 0.1% to approximately 1%. In some implementations, the water-based liquid may include up to approximately 10% cyclodextrin. For example, in some implementations the percentage cyclodextrin in the water-based liquid may be in the inclusive range of approximately 3% to 5%. In still other implementations, the aerosol precursor composition may be a combination of a glycerol-based liquid and a water-based liquid. For example, some implementations may include up to approximately 50% water and less than approximately 20% glycerol. The remaining components may include one or more of propylene glycol, flavorants, nicotine, cyclodextrin, etc. Some examples of water-based liquid compositions that may be suitable are disclosed in GB 1817863.2, filed Nov. 1, 2018, titled Aerosolisable Formulation; GB 1817864.0, filed Nov. 1, 2018, titled Aerosolisable Formulation; GB 1817867.3, filed Nov. 1, 2018, titled Aerosolisable Formulation; GB 1817865.7, filed Nov. 1, 2018, titled Aerosolisable Formulation; GB 1817859.0, filed Nov. 1, 2018, titled Aerosolisable Formulation; GB 1817866.5, filed Nov. 1, 2018, titled Aerosolisable Formulation; GB 1817861.6, filed Nov. 1, 2018, titled Gel and Crystalline Powder; GB 1817862.4, filed Nov. 1, 2018, titled Aerosolisable Formulation; GB 1817868.1, filed Nov. 1, 2018, titled Aerosolised Formulation; and GB 1817860.8, filed Nov. 1, 2018, titled Aerosolised Formulation, each of which is incorporated by reference herein in its entirety.

In some implementations, the aerosol precursor composition may incorporate nicotine, which may be present in various concentrations. The source of nicotine may vary, and the nicotine incorporated in the aerosol precursor composition may derive from a single source or a combination of two or more sources. For example, in some implementations the aerosol precursor composition may include nicotine derived from tobacco. In other implementations, the aerosol precursor composition may include nicotine derived from other organic plant sources, such as, for example, non-tobacco plant sources including plants in the Solanaceae family. In other implementations, the aerosol precursor composition may include synthetic nicotine. In some implementations, nicotine incorporated in the aerosol precursor composition may be derived from non-tobacco plant sources, such as other members of the Solanaceae family. The aerosol precursor composition may additionally or alternatively include other active ingredients including, but not limited to, botanical ingredients (e.g., lavender, peppermint, chamomile, basil, rosemary, thyme, *eucalyptus*, ginger, *cannabis, ginseng*, maca, and tisanes), melatonin, stimulants (e.g., caffeine, theine, and guarana), amino acids (e.g., taurine, theanine, phenylalanine, tyrosine, and tryptophan) and/or pharmaceutical, nutraceutical, nootropic, psychoactive, and medicinal ingredients (e.g., vitamins, such as B6, B12, and C and cannabinoids, such as tetrahydrocannabinol (THC) and cannabidiol (CBD)). It should be noted that the aerosol precursor composition may comprise any constituents, derivatives, or combinations of any of the above.

As noted herein, the aerosol precursor composition may comprise or be derived from one or more botanicals or constituents, derivatives, or extracts thereof. As used herein, the term "botanical" includes any material derived from plants including, but not limited to, extracts, leaves, bark, fibres, stems, roots, seeds, flowers, fruits, pollen, husk, shells or the like. Alternatively, the material may comprise an active compound naturally existing in a botanical, obtained synthetically. The material may be in the form of liquid, gas, solid, powder, dust, crushed particles, granules, pellets, shreds, strips, sheets, or the like. Example botanicals are tobacco, *eucalyptus*, star anise, hemp, cocoa, *cannabis*, fennel, lemongrass, peppermint, spearmint, rooibos, chamomile, flax, ginger, *Ginkgo biloba*, hazel, hibiscus, laurel, licorice (liquorice), matcha, mate, orange skin, *papaya*, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, *curcuma*, turmeric, sandalwood, cilantro, bergamot, orange blossom, myrtle, cassis, valerian, pimento, mace, damien, marjoram, olive, lemon balm, lemon basil, chive, *carvi, verbena*, tarragon, geranium, mulberry, *ginseng*, theanine, theacrine, maca, ashwagandha, damiana, guarana, chlorophyll, baobab or any combination thereof. The mint may be chosen from the following mint varieties: Mentha Arventis, Mentha c.v., Mentha niliaca, *Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens.*

As noted above, in various implementations, the aerosol precursor composition may include a flavorant or materials that alter the sensory or organoleptic character or nature of the aerosol of the smoking article. In some implementations, the flavorant may be pre-mixed with the liquid. In other implementations, the flavorant may be delivered separately downstream from the atomizer as a main or secondary flavor. Still other implementations may combine a pre-mixed flavorant with a downstream flavorant. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime, lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, *ginseng*, chamomile, turmeric, bacopa monniera, gingko *biloba*, withania somnifera, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As used herein, the terms "flavor," "flavorant," "flavoring agents," etc. refer to materials which, where local regulations permit, may be used to create a desired taste, aroma, or other somatosensorial sensation in a product for adult consumers. They may include naturally occurring flavor materials, botanicals, extracts of botanicals, synthetically obtained materials, or combinations thereof (e.g., tobacco, *cannabis*, licorice (liquorice), *hydrangea*, eugenol, Japanese white bark *magnolia* leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, *papaya*, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, *betel*, shisha, pine, honey essence, rose oil, vanilla, lemon oil, orange oil, orange blossom, cherry blossom, *cassia*, caraway, cognac, jasmine, ylang-ylang, sage, fennel, wasabi, piment, ginger, coriander, coffee, hemp, a mint oil from any species of the genus Mentha, *eucalyptus*, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, *curcuma*, cilantro, myrtle, cassis, valerian, pimento, mace, damien, marjoram, olive, lemon balm, lemon basil, chive, *carvi, verbena*, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas.

In some implementations, the flavor comprises menthol, spearmint and/or peppermint. In some embodiments, the flavor comprises flavor components of cucumber, blueberry, citrus fruits and/or redberry. In some embodiments, the flavor comprises eugenol. In some embodiments, the flavor comprises flavor components extracted from tobacco. In some embodiments, the flavor comprises flavor components extracted from *cannabis*.

In some implementations, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to, eucolyptol or WS-3.

The selection of such further components may be variable based upon factors such as the sensory characteristics that are desired for the smoking article, and the present disclosure is intended to encompass any such further components that are readily apparent to those skilled in the art of tobacco and tobacco-related or tobacco-derived products. See, Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties.

In the depicted implementation, the aerosolized aerosol precursor composition includes one more propellants in addition to one or more of the aerosol precursor composition ingredients or components described above. For example, in one implementation, the propellant may comprise a gas hydrofluoroalkane (HFA) 134a (1,1,1,2-tetrafluoroethane). In some implementations, the propellant may comprise HFA 227. In other implementations, a variety of other propellants may be used. As noted above, in addition to the propellant the canister may include various other ingredients including one or more solvents, flavorants, emulsifiers, etc.

In one or more implementations, the present disclosure may be directed to kits that provide a variety of components as described herein. For example, a kit may comprise a mouthpiece with one or more aerosol canisters. A kit may further comprise an aerosol canister with one or more mouthpieces. A kit may further comprise, a plurality of mouthpieces and a plurality of aerosol canisters. A kit may further comprise a plurality of aerosol delivery devices (each comprising, for example, a mouthpiece and an aerosol canister). The inventive kits may further include a case (or other packaging, carrying, or storage component) that accommodates one or more of the further kit components. The case could be a reusable hard or soft container. Further, the case could be simply a box or other packaging structure.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol delivery device comprising:

an aerosol canister comprising a reservoir and a metering valve, the reservoir containing pressurized aerosol that includes an aerosol precursor composition;

a mouthpiece configured to be secured to the aerosol canister; and an actuating assembly configured to actuate the metering valve to release at least a portion of the pressurized aerosol, wherein the actuating assembly is located in the mouthpiece, wherein the actuating assembly comprises a button and an actuator, and wherein the actuating assembly is configured to transform a button force applied to the button along a first path into an actuating force applied by the actuator along a second path, the first and second paths being noncollinear, and further comprising a nozzle insert that includes an ejection port opening and at least one closed and recessed ejection channel, wherein the ejection port opening is positioned in an approximate radial center of the nozzle insert, and wherein the at least one closed and recessed ejection channel is configured to direct the pressurized aerosol into and through the ejection port opening.

2. The aerosol delivery device of claim 1, wherein the first and second paths are substantially orthogonal with respect to each other.

3. The aerosol delivery device of claim 1, wherein the actuating assembly transforms the button force into the actuating force via one or more gears.

4. The aerosol delivery device of claim 1, wherein the button of the actuating assembly comprises at least one button gear rack, wherein the actuator of the actuating assembly comprises at least one actuator gear rack, and wherein the actuating assembly further includes at least one pinion gear configured to engage the at least one button gear rack and the at least one actuator gear rack to translate the actuator along the second path upon movement of the button along the first path.

5. The aerosol delivery device of claim 1, wherein the button of the actuating assembly comprises a pair of button gear racks, wherein the actuator of the actuating assembly comprises a pair of actuator gear racks, wherein the actuating assembly further includes a pair of pinion gears, and wherein each pinions gear is configured to engage a respective button gear rack and a respective actuator gear rack to translate the actuator along the second path upon movement of the button along the first path.

6. The aerosol delivery device of claim 5, wherein the button further includes at least one guide slot, wherein the actuating assembly further includes at least one guide pin, and wherein the guide pin and the guide slot are configured to guide the button along the first path.

7. The aerosol delivery device of claim 1, wherein the nozzle insert is configured to be inserted into an aerosol channel of the actuator.

8. The aerosol delivery device of claim 1, wherein the nozzle insert includes a substantially conical ejection port terminating at the ejection port opening.

9. The aerosol delivery device of claim 8, wherein the at least one closed and recessed ejection channel comprises at least three closed and recessed ejection channels, each of the closed and recessed ejection channels being configured to direct the pressurized aerosol into and through the ejection port.

10. The aerosol delivery device of claim 9, wherein the at least three closed and recessed ejection channels comprise a staggered radial arrangement, wherein respective center axes of the closed and recessed ejection channels are non-coincident with a center of the ejection port opening.

11. The aerosol delivery device of claim 1, wherein the mouthpiece includes a diverter located between the metering valve and an outlet of the mouthpiece.

12. The aerosol delivery device of claim 11, wherein the diverter comprises a substantially V-shaped leading edge.

13. The aerosol delivery device of claim 11, wherein the diverter comprises a substantially V-shaped trailing edge.

14. The aerosol delivery device of claim 11, wherein the diverter comprises a substantially V-shaped leading edge and a substantially V-shaped trailing edge, and wherein the substantially V-shaped leading edge is convex with respect to the direction of flow of the pressurized aerosol and the substantially V-shaped trailing edge is concave with respect to a direction of flow of the pressurized aerosol.

15. The aerosol delivery device of claim 1, wherein the mouthpiece is secured to the aerosol canister via a pair of securing pins that extend through the mouthpiece.

16. The aerosol delivery device of claim 1, wherein the mouthpiece and the aerosol canister are substantially longitudinally aligned.

17. The aerosol delivery device of claim 1, wherein the button is configured to rotate relative to the mouthpiece.

18. The aerosol delivery device of claim 1, wherein the actuator is configured to rotate relative to the mouthpiece.

* * * * *